United States Patent [19]

Bonniface et al.

[11] Patent Number: 5,672,786
[45] Date of Patent: Sep. 30, 1997

[54] PRODUCTION OF DIFLUOROMETHANE

[75] Inventors: David William Bonniface; John David Scott, both of Cheshire; Michael John Watson, Chester, all of United Kingdom

[73] Assignee: Imperial Chemical Industries PLC, United Kingdom

[21] Appl. No.: 507,429

[22] PCT Filed: Mar. 14, 1994

[86] PCT No.: PCT/GB94/00497

§ 371 Date: Sep. 6, 1995

§ 102(e) Date: Sep. 6, 1995

[87] PCT Pub. No.: WO94/21579

PCT Pub. Date: Sep. 29, 1994

[30] Foreign Application Priority Data

Mar. 24, 1993 [GB] United Kingdom .................. 9306072
Mar. 24, 1993 [GB] United Kingdom .................. 9306089

[51] Int. Cl.$^6$ .................................................. C07C 17/08
[52] U.S. Cl. .......................... 570/165; 570/166; 570/167; 570/168; 570/169
[58] Field of Search ........................ 570/165, 166, 570/167, 168, 169

[56] References Cited

U.S. PATENT DOCUMENTS

| 2,744,148 | 5/1956 | Ruh et al. | |
| 2,745,886 | 5/1956 | Ruh et al. | |
| 5,208,395 | 5/1993 | Elsheikh | 570/166 |
| 5,495,057 | 2/1996 | Nam et al. | 570/167 |
| 5,569,795 | 10/1996 | Tsuji et al. | 570/168 |

*Primary Examiner*—Alan Siegel

[57] ABSTRACT

A process for the production of difluoromethane comprising (a) contacting dichloromethane with hydrogen fluoride in the presence of a fluorination catalyst to produce a product stream comprising difluoromethane, monochloromonofluoromethane and unreacted starting materials and (b) separating difluoromethane from the product stream from step (a), wherein sufficient hydrogen fluoride is employed in the process such that during step (b) the molar ratio of hydrogen fluoride to monochloromonofluoromethane is at least about 100:1.

10 Claims, No Drawings

PRODUCTION OF DIFLUOROMETHANE

This application is a 377 of PCT/GB94/00497 filed Mar. 14, 1994, now abandoned.

This invention relates to a process for the production of difluoromethane.

In recent years there has been increasing international concern that chlorofluorocarbons, which are used on a large scale around the world, may be damaging the earth's protective ozone layer and there is now in place international legislation to ensure that their manufacture and use is completely phased out. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned damaging effect on the ozone layer. One approach in the search for suitable replacements has centred on fluorocarbons which do not contain chlorine but which contain hydrogen. The hydrofluorocarbon difluoromethane, also known as HFA 32, is of interest as one such replacement, in particular in a blend thereof with other hydrofluoroalkanes, for example HFA 134a and HFA 125, as a replacement for R-22 and R-502 in refrigeration, air-conditioning and other applications.

Processes have been proposed for the production of difluoromethane. Thus, in U.S. Pat. No. 2,744,148, there is described a process for the production of difluoromethane comprising contacting dichloromethane with hydrogen fluoride in the presence of a fluorination catalyst which comprises nickel, chromium, cobalt, copper or palladium carried on aluminium fluoride. Many other catalysts have been proposed for use in the hydrofluorination of dichloromethane, for example, chromium fluoride on alumina in U.S. Pat. No. 4,147,733; aluminium fluoride, chromium fluoride, mixtures thereof, aluminium fluoride on active carbon or ferric chloride on active carbon in EP 128510; chromium oxyfluoride in U.S. Pat. No. 2,745,886 and chromia in GB 1,307,224.

However, a serious problem with the production of difluoromethane by the hydrofluorination of dichloromethane is that a substantial amount of a highly toxic by-product, monochloromonofluoromethane, HCFC 31, is produced as an intermediate. HCFC 31 has an estimated Occupational Exposure Limit of 10 parts per billion, and may be produced in substantial quantities, indeed as much as 20% or more of the product from the hydrofluorination of dichloromethane.

We have now found that, rather than following the obvious course in finding a solution to this problem, that is to search for conditions under which the production of HCFC 31 is reduced, the problem may be solved by suppressing the toxicity problems associated with the HCFC 31 which is produced.

According to the present invention there is provided a process for the production of difluoromethane comprising: (a) contacting dichloromethane with hydrogen fluoride in the presence of a fluorination catalyst to produce a product stream comprising difluoromethane, monochloromonofluoromethane and unreacted starting material and (b) separating difluoromethane from the product stream from step (a), wherein sufficient hydrogen fluoride is employed in the process such that during step (b) the molar ratio of hydrogen fluoride to monochloromonofluoromethane is at least about 100:1.

Preferably during step (b) the molar ratio of hydrogen fluoride to monochloromonofluoromethane is at least about 150:1, more preferably at least about 200:1 and especially at least about 300:1.

The Occupational Exposure Limit (O.E.L.) for HCFC 31 is estimated at 10 parts per billion, whilst that for hydrogen fluoride is 3 parts per million. Whilst hydrogen fluoride is therefore toxic, it is estimated to be about 300 times less toxic than HCFC 31. Furthermore, the toxicity problems associated with hydrogen fluoride usually exist in reactions in which it is employed as the reagent, and in particular where it is employed in hydrofluorination reactions. Thus, it has been the toxicity of hydrogen fluoride which has determined the safety requirements and thus costs associated with conventional hydrofluorination reactions.

The high toxicity of HCFC 31 however, produced in substantial quantities during the hydrofluorination of dichloromethane would exceed the toxicity of hydrogen fluoride in the process streams, thereby increasing the safety requirements, for example the use of specialist high sensitivity equipment for detecting very low levels of HCFC 31, and thus costs of carrying out the hydrofluorination of dichloromethane.

We have found that where hydrogen fluoride is employed in sufficient quantity, then it may effectively reduce the problem of HCFC 31 by enhancing conversion of HCFC 31 to HFA 32 and at the same time diluting the HCFC 31 to concentrations below 30 ppb such that the highest concentration of HCFC 31 at any point in the process is less than 30 ppb, preferably less than 10 ppb and especially less than 3 ppb. In this way, the predominant toxicity problem to be faced and monitored is that of hydrogen fluoride. Consequently, the equipment or plant in which the process is effected may be operated safely with respect to both hydrogen fluoride and HCFC 31 when it is provided with a system for monitoring and detecting levels of hydrogen fluoride below 5 parts per million.

In particular, the concentration of HCFC 31 may tend to increase during the separation of difluoromethane from the process stream, step (b) of the process, thereby causing a localised high concentration of HCFC 31. However, hydrogen fluoride remains with the HCFC 31 and thus if sufficient hydrogen fluoride is present in step (b), then this localised concentration of HCFC 31 may be maintained at an acceptable level.

Typically the separation step (b) is performed using distillation and difluoromethane and hydrogen chloride are recovered from the bottom of the distillation column whilst excess hydrogen fluoride, HCFC 31, and unreacted dichloromethane are obtained from the top of the column and recycled.

According to a preferred embodiment of the present invention there is provided a process for the production of difluoromethane comprising: (a) contacting dichloromethane with hydrogen fluoride in the presence of a fluorination catalyst to produce a product stream comprising difluoromethane, monochloromonofluoromethane and unreacted starting materials, (b) separating difluoromethane from the product stream from step (a) and (c) recovering difluoromethane and recycling HCFC 31 to step (a) wherein sufficient hydrogen fluoride is employed in the process such that during step (b) the molar ratio of hydrogen fluoride to monochloromonofluoromethane is at least about 100:1.

Usually, where sufficient hydrogen fluoride is employed such that the ratio of hydrogen fluoride to monochloromonofluoromethane is at least 100:1 in step (b), the ratio of hydrogen fluoride to HCFC 31 will also be at least 100:1 for step (c) and step (a).

The amount of hydrogen fluoride which is required in order to achieve the required ratio of hydrogen fluoride to HCFC 31 will depend upon the conversion of dichloromethane and the selectivity to HCFC 31 and HFA 32, that is the amount of HCFC 31 produced in step (a) of the process, which depends inter alia upon the conditions of temperature and pressure under which the process is operated and the choice of catalyst.

Furthermore, it is not essential that all the hydrogen fluoride is passed over the catalyst. Thus additional hydrogen fluoride may, as required, be added to the process stream recovered from step (a) of the process in order to ensure that the required ratio of hydrogen fluoride to HCFC 31 is achieved in step (b). Preferably however, the process is provided with a single hydrogen fluoride feed to step (a).

Overall, the molar ratio of hydrogen fluoride to dichloromethane which is fed to the process will be at least 5:1, and usually more than 10:1. There is generally no need to use more than about 100:1 and the molar ratio of hydrogen fluoride to dichloromethane will usually be less than about 50:1. Where the yield of HCFC 31 in step (a) of the process is about 10%, the ratio of hydrogen fluoride to dichloromethane may be at least 10:1, whilst where the yield of HCFC 31 is step (a) is 5%, the ratio of hydrogen fluoride to dichloromethane may be at least 5:1. Typically however, the yield of HCFC 31 may be as much as 15%.

The process is preferably operated on a continuous basis, with make-up hydrogen fluoride being fed to step (a) of the process and recycled HCFC 31 and unreacted dichloromethane being converted to HFA 32 in step (a) of the process.

The conditions of temperature and pressure and choice of catalyst employed in step (a) may be as described in the prior art, for example a temperature in the range from about 100° C. to about 500° C., preferably from about 200° C. to about 400° C. Atmospheric pressure may be employed, although superatmospheric pressure, say up to about 30 bar, or subatmospheric pressures may be employed if desired. The catalyst may be a conventional fluorination catalyst, for example a catalyst based on chromia, chromium fluoride or chromium oxyfluoride, alumina, aluminium fluoride or aluminium oxyfluoride, or a catalyst comprising a metal, for example nickel, cobalt, zinc, iron or copper supported upon chromia, magnesia and/or alumina.

We have further found that a fluorination catalyst comprising zinc or a compound of zinc and a metal oxide, fluoride or oxyfluoride may be employed to increase the selectivity of the process towards difluoromethane with a consequent decrease in the yield of HCFC 31 from the process. The increased selectivity to difluoromethane provides a substantial benefit in reducing the levels of HCFC 31 produced, and thus allows less hydrogen fluoride to be employed whilst providing the molar ratio of hydrogen fluoride to HCFC 31 required by the present invention.

We prefer to employ a catalyst as described in one of EP 0502605 or PCT/GB93/00244, the disclosures of which are incorporated herein by reference.

Thus the metal of the metal oxide, fluoride or oxyfluoride, the amount of zinc, the catalyst preparation method, the catalyst prefluorination treatment, the form of the catalyst, catalyst regeneration treatment, and the presence of other metals or compounds thereof in the catalyst may be as described for the catalysts in EP 0502605 or PCT/GB93/0024, the disclosures of which are incorporated herein by reference. We especially prefer a catalyst as described in EP 0502605.

Use of the preferred catalyst generally allows lower temperatures to be used than those employed in the prior art whilst the level of HCFC 31 produced may not be increased compared with the levels of HCFC 31 produced at higher temperatures using catalysts previously proposed. The use of lower temperatures results in substantially longer catalyst lifetimes with a consequent reduction in the frequency with which the catalyst requires regeneration. The temperature is especially preferably in the range from about 170° C. to about 340° C., and particularly in the range from about 240° C. to about 320° C.

The invention is illustrated but not limited by the following example.

EXAMPLE 10 g of a zinc/chromium mixed oxide catalyst prepared by co-precipitation and comprising 8% by weight zinc was charged to a ½" diameter Inconel reactor tube and heated to 300° C. in nitrogen. Hydrogen fluoride was then passed over the catalyst for 24 hours at 300° C. and the reactor was then cooled to 250° C.

The reactor was pressurised to 10 bar in nitrogen, and dichloromethane and hydrogen fluoride were passed over the catalyst in the mole ratios indicated in Table 1. The vent gas from the reactor was scrubbed with water to remove hydrogen fluoride and hydrogen chloride, sampled and analysed by Gas Chromatography. The results are shown in Table 1.

TABLE 1

| $HF:CH_2Cl_2$ | Off Gas Composition (% v/v) | | | $HF:CH_2FCl$ Off Gas |
|---|---|---|---|---|
| (Mole ratio) | $CH_2Cl_2$ | $CH_2ClF$ | $CH_2F_2$ | Mole Ratio |
| 27.1 | 1.0 | 7.1 | 92.0 | 391 |
| 21.3 | 2.3 | 10.0 | 87.7 | 213 |
| 19.6 | 2.8 | 11.1 | 86.1 | 175 |
| 12.5 | 7.4 | 9.4 | 83.1 | 123 |

EXAMPLE 2 and 3

The procedure of example 1 was repeated except that the examples were performed at atmospheric pressure and the temperature and feed ratio of hydrogen fluoride to dichloromethane were as stated in Table 2 below. The results are also shown in Table 2 below.

TABLE 2

| $HF:CH_2Cl_2$ | Temp | Off Gas Composition (% v/v) | | | $HF:CH_2FCl$ Off-Gas |
|---|---|---|---|---|---|
| (Mole ratio) | (°C.) | $CH_2Cl_2$ | $CH_2ClF$ | $CH_2F_2$ | Mole Ratio |
| (Example 2) 15.9 | 250 | 3.5 | 5.2 | 91.3 | 271 |
| (Example 3) 16.1 | 200 | 34.7 | 11.3 | 54.0 | 134 |

EXAMPLE 4 to 7

The procedure of examples 2 and 3 was repeated except that the catalysts employed were as follows:

Example 4: Chromia having a surface area of 160 m²/g.

Example 5: 2% w/w zinc on alumina prepared by impregnating gamma alumina having an initial surface area of 180 m²/g with aqueous zinc chloride solution.

Examples 6 and 7: 2% w/w chromium on alumina prepared by impregnating gamma alumina having an initial surface area of 180 m²/g with aqueous chromium chloride solution.

The conditions and results for example 4 to 7 are shown in Table 3 below.

TABLE 3

| HF:CH$_2$Cl$_2$ (Mole ratio) | Temp (°C.) | Off Gas Composition (% v/v) | | | HF:CH$_2$FCl Off-Gas Mole Ratio |
|---|---|---|---|---|---|
| | | CH$_2$Cl$_2$ | CH$_2$ClF | CH$_2$F$_2$ | |
| (Example 4) 15.9 | 200 | 75.8 | 14.0 | 10.2 | 105 |
| (Example 5) 16.9 | 200 | 64.1 | 15.6 | 20.3 | 107 |
| (Examples 6 and 7) | | | | | |
| 12.8 | 200 | 89.5 | 8.7 | 1.8 | 149 |
| 15.2 | 200 | 91.8 | 7.0 | 1.2 | 218 |

We claim:

1. A process for the production of difluoromethane comprising (a) contacting dichloromethane with hydrogen fluoride in the presence of a fluorination catalyst to produce a product stream comprising difluoromethane, monochloromonofluoromethane and unreacted starting materials and (b) separating difluoromethane from the product stream from step (a), wherein sufficient hydrogen fluoride is employed in the process such that during step (b) the molar ratio of hydrogen fluoride to monochloromonofluoromethane is at least about 100:1.

2. A process as claimed in claim 1 in which the molar ratio of hydrogen fluoride to monochloromonofluoromethane is at least about 150:1.

3. A process as claimed in claim 1 in which additional hydrogen fluoride is added to the process stream recovered from step (a) in order to ensure that the required ratio of hydrogen fluoride to HCFC 31 is achieved during step (b).

4. A process for the production of difluoromethane comprising (a) contacting dichloromethane with hydrogen fluoride in the presence of a fluorination catalyst to produce a product stream comprising difluoromethane, monochloromonofluoromethane and unreacted starting materials, (b) separating difluoromethane from the product stream from step (a) and (c) recovering difluoromethane and recycling HCFC 31 to step (a) wherein sufficient hydrogen fluoride is employed in the process such that during step (b) the molar ratio of hydrogen fluoride to monochloromonofluoromethane is at least about 100:1.

5. A process as claimed in any one of claims 1 to 4 in which the separation step (b) comprises distilling the product stream from step (a) whereby to separate a bottom stream comprising difluoromethane and hydrogen chloride from a top stream comprising hydrogen fluoride, HCFC 31 and unreacted dichloromethane.

6. A process as claimed in any one of claims 1 to 5 in which the fluorination catalyst comprises a metal oxide, metal fluoride or oxyfluoride.

7. A process as claimed in claim 6 in which the metal of the oxide, fluoride or oxyfluoride is at least one of chromium, aluminium, zinc, nickel, cobalt, copper and magnesium.

8. A process as claimed in claim 7 in which the catalyst comprises zinc or a compound of zinc and a metal oxide, fluoride or oxyfluoride in which the metal of the oxide, fluoride or oxyfluoride is chromium or aluminium.

9. A process as claimed in any one of claims 1 to 8 when carried in equipment provided with a system for monitoring and detecting concentrations of hydrogen fluoride below 5 parts per million.

10. A process as claimed in claim 9 in which step (a) is effected at a temperature in the range from about 240° C. to about 320° C.

* * * * *